Figure 1:
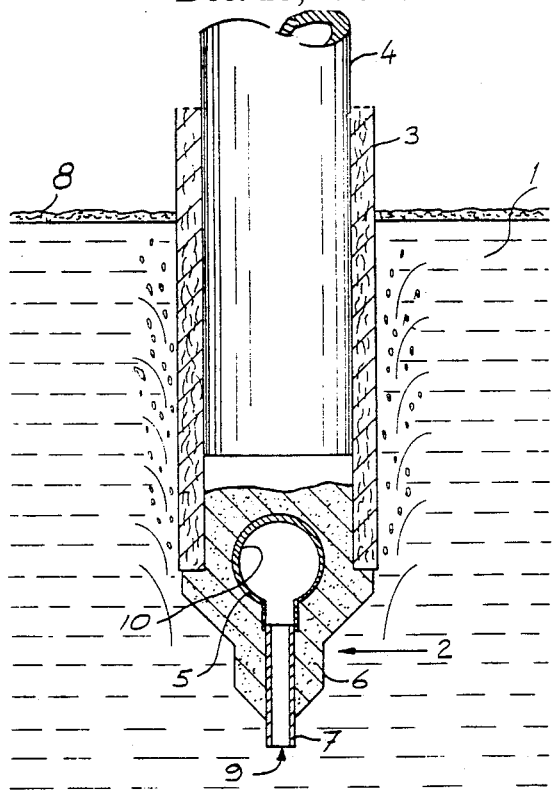

United States Patent [19]

Kumbrant et al.

[11] Patent Number: 4,489,604
[45] Date of Patent: Dec. 25, 1984

[54] APPARATUS FOR TESTING AND TAKING SAMPLES FROM LIQUID METAL

[75] Inventors: Lars Kumbrant, Orsundsbro; Gunnar Olofsson; Mats Larsson, both of Laxa, all of Sweden

[73] Assignee: Rockwool Aktiebolaget, Skovde, Sweden

[21] Appl. No.: 406,371

[22] Filed: Aug. 9, 1982

[30] Foreign Application Priority Data

Aug. 31, 1981 [SE] Sweden .............................. 8105033

[51] Int. Cl.³ .............................................. G01N 1/12
[52] U.S. Cl. ............................. 73/432 R; 73/864.59; 252/62; 374/140
[58] Field of Search ........... 73/864.53, 864.54, 864.55, 73/864.56, 864.57, 864.58, 864.59, DIG. 9; 374/140; 239/589; 252/62

[56] References Cited

U.S. PATENT DOCUMENTS

| | | | |
|---|---|---|---|
| 3,353,808 | 11/1967 | Norburn | 374/140 |
| 3,457,790 | 7/1969 | Hackett | 73/864.56 |
| 3,709,040 | 1/1973 | Coe | 73/DIG. 9 |
| 4,172,042 | 10/1979 | Kiisler | 252/62 |
| 4,197,745 | 4/1980 | Kumbrant | 73/864.53 |

Primary Examiner—S. Clement Swisher

[57] ABSTRACT

Equipment for testing or test sampling liquid metal by introducing a protection sleeve (3; 3'; 3") together with a testing or sampling means (2; 11) provided inside the protection sleeve. The protection sleeve comprises a thermoinsulating tube (3; 3'; 3") made of synthetic amorphous mineral fibers, preferably fibres of diabase type and having a sagging point of 1,000°–1,200° C. according to the standards of the Swedish Institute for Materials Testing, and bound with an evenly distributed binder comprising or including among other things a binder component of organic type, for instance a thermosetting resin like phenol resin, carbamide resin or melamine resin and/or substances incorporated in the fiber material, for instance crystal water containing salts or carbonates which at the temperature of the liquid metal spontaneously and successively emit gases. The mineral fibre tube (3; 3'; 3") can be manufactured from mineral fibres having an original weight per unit of volume of 20–70 kg/m3, which have been compressed to a weight per unit of volume of 200–800 or preferably 500–700 kg/m3. Preferably the binder is added in an amount of 2–8 % by weight. The intensity of the turbulent flow in the molten metal is controlled by varying the amount of binder in the thermoinsulating mineral fibre tube and/or by varying the hardness of the mineral fibre tube.

12 Claims, 3 Drawing Figures

APPARATUS FOR TESTING AND TAKING SAMPLES FROM LIQUID METAL

The present invention generally relates to a method and an apparatus for testing and taking test samples from or making measurements in liquid iron, steel or any other metal or metal alloy, and the invention is more particularily concerned with an apparatus for protecting the testing and sampling equipment against the heat from the molten metal.

For determinating certain parameters of a liquid metal, for instance the temperature of the molten metal, the content of oxygen, carbon or different alloy materials, a test is made or a test sample is taken in that a lancet having a testing or sampling equipment at the end thereof is introduced into the liquid metal. By modern methods the test can be made or the sample can be taken within the course of about 6-8 seconds, but the liquid metal generally has a substantially higher temperature than the lancet and some testing or sampling equipment can stand even for the said relatively short period of time such parts have to be protected against the heat of the molten metal.

For protecting the lancet and the sampling equipment it is known to make use of a sleeve of compressed cardboard which is mounted round the portion of the lancet with the sampling equipment which is to be introduced, into the molten metal.

When introducing the lancet with the cardboard sleeve in the liquid metal moisture is separated from the cardboard sleeve in the form of water steam. At the same time the cardboard sleeve is burnt and becomes charred whereby in addition thereto gases are developed. The said gases cause a heavy turbulent flow or cooking around the cardboard sleeve. Such heavy cooking makes the molten metal splash and sputter which creates a serious risk of accident for the operator of the testing or sampling equipment. Since cardboard is relatively heavily hydroscopic the cardboard sleeve normally contains some amount of water.

In order to avoid the disadvantages involved in a protection sleeve of cardboard it has been suggested to form the protection sleeve of a fire proof material for instance a fire proof fibrous wool material. Since molten steel often has a temperature of 1600°-1800° C. the fire proof fibrous wool must be of a type which is able to stand such temperature for at least 6-8 seconds which are needed for taking the test or sample. The said fibrous wool material is expensive and it may often be difficult to design or mount the fibrous wool, so as to provide a solid protection sleeve which thermally protects the lancet and the testing or sampling equipment and at the same time allows a movement of the liquid metal around the testing or sampling equipment.

A protection sleeve of refractory or fire proof material gives no or practically no turbulent flow or cooking around the protection sleeve and the disadvantage of heavy cooking and splashing as when using the cardboard sleeve is thereby eliminated. Also the fire proof fibrous wool does not add carbon or any other substances to the liquid metal which may adversely effect the result of the analysis of the sample which has been taken.

It has, however, been shown that in some cases a large scattering of the test values and sometimes obvious false values are obtained. It is supposed that the reason therefor is that the molten metal around the protection sleeve moves in a laminar flow passing along the surfaces of the protection sleeve, the lancet and the sampling equipment, whereby the molten metal is cooled and possibly subjected to structural changes before reaching the sampling equipment. It has especially been shown that the scattering of the results when measuring the temperature of a liquid metal by means of a protection sleeve of refractory or fire proof material is very large. While normally an accuracy of measurement for the temperature of about ±1° C. is supposed to be obtained when measuring liquid metal at about 1550° C., it has been shown that a scattering of the measured temperature of about 10°-20° C. results when using a protection sleeve of refractory or fire proof material. Consequently a false value of the temperature is obtained which can be of great importance for guiding the quality of the liquid metal.

It has consequently been shown that some turbulent movement or cooking around the protection sleeve during the sampling is advantageous or even necessary for giving a good and safe result. Such cooking, however, must take place under controlled conditions and no substantial amount of carbon or any other substances which may adversely effect the test results are allowed to be introduced into the liquid metal.

According to the invention the protection sleeve is made of a material which does not burn in the same way as a cardboard sleeve and which is also not directly fire proof like a sleeve made of fire proof fibrous wool. The movement or cooking of the molten metal also should be relatively constant during the entire period of testing or sampling irrespective of the fact that the protection sleeve successively melts or is consumed in any other way.

According to the invention it is therefore suggested that the protection sleeve be made of a material which does not burn but melts at reasonable speed in the liquid metal and which during the melting successively develops gases providing a predetermined bubbling or cooking and thereby a turbulent flow round the protection sleeve in the molten metal. A particularly suitable material for this purpose has proved to be a compressed material of synthetic amorphous mineral fibres having a sagging point of less than about 1200° C. as measured according to the method stipulated by the National Swedish Institute for Materials Testing. and which comprises a binder which is evenly distributed in the material and which is decomposed at the temperature of the liquid metal while developing gas bubbles. The mineral fibres may be bound by different tpes of binders, but preferably at least some portion of the binder should be of the organic type, preferably a thermosetting resin such as phenol resin, carbamide resin or melamine resin. At the manufacture of said mineral fibres, they normally obtain a weight by unit of volume of about 20-70 kg/m3, and for providing a stable protection sleeve having a suitable consumption in the liquid metal the mineral fibre preferably should be compressed to a weight by unit of volume of about 200-800 or preferably 500-700 kg/m3.

Since the mineral fibres only successively melt in the liquid metal the fibrous material can be considered substantially inert and what provides the intended bubbling or cooking is a binder. By an intimate mixing of mineral fibres with a suitable amount of binder it is thereby possible to foresee a cooking which is controlled and can be predetermined and which is substantially constant independently of the consumption of the protection sleeve during the course of sampling. Consequently the gas developing binder determines the amount of bubbling or cooking. A suitable addition of the organic binder is 2-8% by weight as calculated on the weight of the ready protection sleeve.

The wall thickness and the hardness of the mineral fibre sleeve is calculated so that the protection sleeve does not melt completely and so that it maintains some intended stability during the course of the testing or sampling. Depending on which metal is to be tested and most importantly the temperature of the actual metal, the amount of organic binder, the weight by volume of the sleeve material and the wall thickness of the sleeve is varied.

According to a preferred further development of the invention the protection sleeve of mineral wool is formed with an inner relatively thin cardboard sleeve which provides an additional bar as a protection for the lancet for instance if the mineral fibre sleeve should be defective or has uneven wallthicknesses which cannot be discovered by the eye. Also the cardboard sleeve can be used to provide a signal that the mineral fibre sleeve has melted down in that a heavy cooking appears as soon as the molten metel penetrates into the cardboard sleeve when the testing or sampling period is exceeded.

Further characteristics of the invention will be evident from the following detailed description in which reference will be made to the accompanying drawings.

In the drawings

FIG. 1 diagrammatically shows an axial cross section through an apparatus for taking an analysis sample of liquid metal and formed with a protection sleeve according to the invention.

Figure 2:
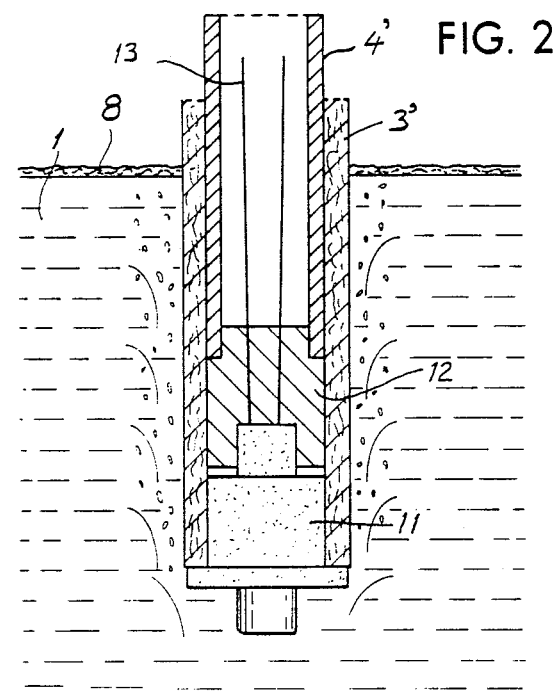

FIG. 2 correspondingly shows an apparatus having a test probe for measuring the temperature of the molten metal and which apparatus likewise is formed with a protection sleeve according to the invention.

Figure 3:
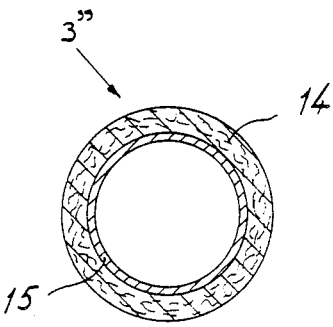

FIG. 3 is a cross section through a modified embodiment of a protection sleeve according to the invention.

The apparatus shown in FIG. 1 for taking analysis samples from a liquid metal bath 1 generally comprises a sampling tip 2 which by means of a protection sleeve 3 is mounted on a lancet 4. In the illustrated case the sampling tip is formed with a shot mould 5 which is moulded in a sampling tip body 6 of sand and into which a refractory tube extends, for instance a tube 7 of quartz glass. The sampling or test equipment, however, can be of any other type, since the type of sampling or testing equipment is out of the area of interest of the invention.

The sampling tip 2 is mounted at the end of the protection sleeve 3, for instance by means of glue, and the protection sleeve 3 in turn is mounted round a lancet 4 by means of which the sampling equipment together with the protection sleeve can be handled during the course of the sampling or testing. The object of the protection sleeve 3 is both to protect the lancet and any other parts of the equipment against damage depending of the high temperature of the liquid metal, and also to provide a turbulent flow in the liquid metal round the protection sleeve and at or adjacent the sampling or testing means which can be a sampling tip as shown in FIG. 1 or a thermo testing element as shown in FIG. 2, an oxygen probe, a pyrometer or similar means.

According to the invention the thermoinsulating sleeve 3 is made of a material which is not fireproof and can be burnt but has a sagging point which is lower than the temperature of the molten metal. By sagging point is meant the temperature as defined by the National Swedish Institute for Materials Testing, at which the material gets a special sagging or softening structure. A material suited for most generally appearing liquid metals is mineral fibres having a sagging temperature of 1000°-1200° C. Preferably synthetic amorphous mineral fibres are used, preferably mineral fibres of diabase type which have a melting temperature of about 1400° C. and which for short periods of time can be subjected to the above mentioned high temperatures without any risk that the material melts too quickly. Mineral fibres of diabase type have a sagging point according to the stipulations of the National Swedish Institute for Materials Testing of between about 1000° and 1200° C.

A normal sampling or testing by the use of modern equipment or a manual sampling or testing takes a time of 6-8 seconds, and the protection sleeve 3 therefore must be able to stand the high temperature of the molten metal for at least such period of time. For obtaining a protection sleeve which is consumed in a suitable time the thermoinsulating sleeve 3 must have a predetermined hardness and a predetermined thickness. When manufactured, mineral fibres normally have a weight per unit of volume of about 20-70 kg/m3, but in order to obtain a suitable hardness for the practice of this invention, the mineral fibres are compressed to a weight per unit of volume of about 200°-800° or 500°-700° C. For keeping the mineral fibres together a binder of a type known per se is used.

In order to obtain the above mentioned turbulent movement of the liquid metal round the protection sleeve 3, the binder, or at least some portion of the binder, is preferably an organic binder which at contact with the molten metal develops gases which give the molten metal a movement in the upward direction which can be controlled and predetermined. in that the binder at least partly is of organic nature. Alternatively, or in addition, the binder may comprise one or more substances incorporated in the fibrous material, for instance crystal water containing salts or carbonates, which at the temperature of the molten metal spontaneously and successively produce gases. As examples of suitable binders can be mentioned thermosetting resins like phenol resin, carbamide resin or melamine resin. The binder should be evenly distributed in the mineral fibre sleeve 3. The sleeve can be manufactured as a solid tube or in the form of two tube halves which are interconnected, and preferably manufacture is such that the mineral fibres are sprinkled with the organic binder during manufacture of the mineral fibre, whereupon the binder is brought to set at the same time as the mineral fibre tube is compressed to the intended weight by volume. By adding larger or smaller amounts of binder it is possible to determine the extent of bubbling or cooking which is intended to appear. A large amount of binder gives a more heavy cooking and a small amount of binder gives a gentle cooking. A suitable addition of the organic binder is 2-8% by weight as calculated on the mineral fibre tube.

The same effect achieved by adding the organic binder to the mineral fibre can alternatively be obtained by adding salts to the mineral fibre, which sales, when contacted by the hot molten metal, emit $H_2O$ or $CO_2$. There are, however, certain difficulties in obtaining a controlled and predeterminable turbulent movement in the molten metal round the protection sleeve, and it is preferred that the mineral fibre material contains an organic binder.

Preferably the sleeves are manufactured with a predetermined minimum amount of binder, and the sleeves are additionally impregnated with further binder or possibly solutions of salt and other substances which emit gases when heated so that the correct gas emittance property is obtained for each specific application.

The desired bubbling or cooking in the liquid metal should be at a limit, where on the one hand there is no longer a laminar flow of the liquid metal round the protection sleeve and on the other hand where there is splashing. As mentioned above the extent of cooking is controlled with reference to the temperature and the type of molten metal by controlling the amount and the type of gas emitting substance in the thermoinsulating sleeve and by controlling the hardness and thereby the consumption capacity of the liquid metal on the protection sleeve. It should be observed that gas emission in most cases is endothermic, and this may be utilized for instance by providing a heavier impregnation of the inner layers of the sleeve than the outer layer or layers.

When using the apparatus shown in FIG. 1, the protection sleeve with the sand mold sampling tip 2 is mounted on the lancet, whereupon the sampling equipment with the tip is introduced in the molten metal 1 through a layer 8 of slag or other impurities. Thereby molten metal flows through the quartz glass tube 7 as shown by arrow 9 and the metal fills the cavity 10 of the mold 5. The hot molten metal, which comes into contact with the outer surface of the protection sleeve 3 successively melts the outermost layers of the thermoinsulating sleeve 3, and at the same time the organic binder of the mineral fibre sleeve is decomposed so that gas bubbles are developed which provide a rising turbulent movement in the molten metal. By the inevitable cooling of the molten metal when the molten metal contacts the protection sleeve there is a tendency for a thin layer of molten metal to flow downwards along the protection sleeve. Depending on the turbulent movement provided by the action of the rising bubbles such movement downwards of the molten metal, however, is prevented and the tubulent movement thereby eliminates the action of the slight cooling of the metal layer just adjacent to the surface of the protection sleeve. Also no particles or substances are capable of flowing down towards the quartz glass tube 7 and the sample taken from the molten metal really becomes representative of the average composition of the molten metal.

Since the organic binder is intimately and evenly distributed in the mineral fibres, a unitary gas formation and cooking is obtained during the course of the sampling or testing following the melting of the mineral fibre tube.

In FIG. 2 there is shown an apparatus for measuring the temperature of the liquid metal. The apparatus comprises a temperature measuring probe 11 which is mounted at the end of a protection sleeve 3' which in turn is mounted on a lancet 4'. At the end of the lancet 4' there are means 12 for connection of the temperature probe 11. From the connection means 12 conduits 13 extend to some suitable instrument for reading the temperature observed by the temperature probe 11.

For getting a correct temperature statement it is of great importance that the layer of molten metal which is cooled by the contact with the protection sleeve 3' is not allowed to flow downwards towards the temperature probe 11, and this is eliminated in that the protection sleeve according to the invention is continuously and to a controlled degree emitting gas bubbles providing a rising turbulent flow of the metal layer closest to the protection sleeve. The cooled metal layer thereby is prevented from flowing down towards the temperature probe.

For certain applications it may be wanted to provide a further improved thermal protection for the lancet or the sampling or test means provided inside the protection sleeve, and for this purpose the protection sleeve 3' as shown in FIG. 3 may be formed as a mineral fibre tube 14 which at the inside thereof carries a thin sleeve 15 of cardboard. Such a cardboard sleeve 15 provides an improved thermal insulation, and the cardboard sleeve further can be used as a last signal of warning that the mineral fibre tube 14 is consumed. Such signal of warning is obtained in that the cooking is accelerated when the molten metal from the outside of the protection sleeve reaches the cardboard sleeve 15. In order not to damage the test means the test equipment is quickly retracted from the molten metal.

It is to be understood that the above specification and the embodiments of the invention shown in the drawings are only illustrating examples and that many different modifications may be presented within the scope of the appended claims.

We claim:

1. In apparatus for testing or sampling a molten metal comprising testing means or sampling means adapted to be immersed into a molten metal, said apparatus including thermal protection means surrounding said testing means or sampling means for protecting said testing means or sampling means from the heat of said molten metal when said apparatus is immersed in said molten metal, the improvement wherein
said thermal protection means comprises mineral wool and a substance distributed in said mineral wool which substance spontaneously decomposes and emits gas and when said substance is contacted with molten metal upon immersion of said apparatus therein.

2. Apparatus according to claim 1 wherein said substance comprises an at least partially organic binder which binds said mineral wool in a unitary mass.

3. Apparatus according to claim 1 wherein said substance comprises a salt or carbonate.

4. Apparatus according to claim 1 wherein said mineral wool has a melting point such that, when contacted by said molten metal, said mineral wool melts at a rate which permits said substance to decompose and emit gas in a pre-determined manner to effect a controlled and pre-determined bubbling effect in molten metal in which said apparatus is immersed.

5. Apparatus according to claim 1 wherein said mineral wool comprises synthetic amorphous mineral fibre of the diabase type having a sagging point of less than about 1200° C. according to the method stipulated by the Swedish Institute for Materials Testing.

6. Apparatus according to claim 2 wherein the mineral wool has a weight per unit volume of 200–800 kg/m$^3$.

7. Apparatus according to claim 6 wherein said mineral wool has a weight per unit of volume of 500–700 kg/m$^3$.

8. Apparatus according to claim 6 or claim 7 wherein said mineral wool is in the form of a tube.

9. Apparatus according to claim 2 wherein the binder comprises a thermosetting resin selected from the group consisting of phenol resin, carbamide resin or melamine resin.

10. Apparatus according to claim 1 wherein said substance is present in an amount of 2–8 percent by weight based on the total weight of the mineral wool.

11. Apparatus according to claim 1 wherein said thermal protection means comprises a plurality of said substances each of a different type and selected to give a pre-determined bubbling effect when immersed in molten metal.

12. Apparatus according to claim 1 wherein said testing means or sampling means is mounted on a lance and wherein said thermal protection means comprises a tube surrounding said testing means or sampling means and at least a portion of said lance and wherein said tube comprises an outer tube comprising said mineral wool and an inner tube comprising cardboard.

* * * * *